United States Patent [19]

Neill et al.

[11] Patent Number: 5,554,364
[45] Date of Patent: Sep. 10, 1996

[54] COMPOSITIONS AND METHODS TO REDUCE POST-PERM ODOR

[75] Inventors: Paul H. Neill, Hinsdale; Loralei Brandt, Cary, both of Ill.

[73] Assignee: Helene Curtis, Inc., Chicago, Ill.

[21] Appl. No.: 484,111

[22] Filed: Jun. 7, 1995

[51] Int. Cl.$^6$ ........................................ A61L 9/01
[52] U.S. Cl. .................. 424/76.1; 424/76.4; 424/70.2
[58] Field of Search .................. 424/76.1, 76.4, 424/70.2

[56] References Cited

U.S. PATENT DOCUMENTS

| | | | |
|---|---|---|---|
| 4,199,562 | 4/1980 | Vanlerberghe et al. | 424/47 |
| 5,071,441 | 12/1991 | Schnetzinger et al. | 424/72 |
| 5,161,553 | 11/1992 | Cohen et al. | 132/205 |

*Primary Examiner*—Thurman K. Page
*Assistant Examiner*—Kathryne E. Shelborne
*Attorney, Agent, or Firm*—Marshall, O'Toole, Gerstein, Murray & Borun

[57] ABSTRACT

Compositions and methods for reducing post perm odors, via reaction with hair aldehydes, by contacting the hair with a polyhydric phenol, particularly resorcinol or its derivatives, before, during, or after application of a reducing agent-containing waving lotion. The polyhydric phenol should have the following formula (I):

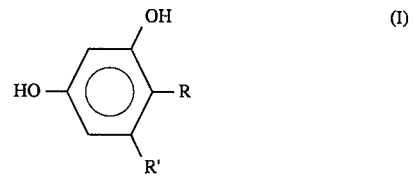

wherein
R'=H or OH,
R=H or $C_1$–$C_{12}$ alkyl,
$C_1$–$C_{12}$ alcohol,
$C_1$–$C_{12}$ aldehyde, or
a ketone having formula (II)

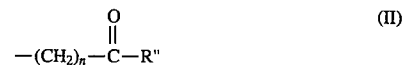

wherein
n=0–12, R"=$C_1$–$C_{12}$ alkyl, and wherein n+number of carbons in R"=1–12.

26 Claims, 7 Drawing Sheets

COMPOSITIONS AND METHODS TO REDUCE POST-PERM ODOR

FIELD OF THE INVENTION

The present invention is directed to compositions and methods for reducing post-perm odors which result from reducing agents used in the hair permanent waving process. More particularly, the present invention is directed to contacting the hair before, during, and/or after application of a waving lotion, with a composition containing a polyhydric phenol, particularly resorcinol or its derivatives, e.g., resorcinol, hexylresorcinol or acetaldehyde resorcinol, to substantially reduce post-perm odors.

BACKGROUND OF THE INVENTION AND PRIOR ART

In general, permanent waving of human hair is achieved by chemically breaking the sulfur-to-sulfur or disulfide cystine bonds occurring naturally in human hair and then reforming the cystine bonds while the hair is wrapped or curled on rods. The sulfur-to-sulfur cystine bonds in human hair maintain the hair in a naturally straight or curly configuration and, in order to permanently reshape the hair into a lasting, different configuration, a significant percentage of the sulfur-to-sulfur bonds must be broken and then reestablished after the hair is reconfigured in a desired position, such as wrapped around a suitable mandrel or roller. In general, the sulfur-to-sulfur cystine bonds are broken with a waving lotion composition, containing a reducing agent, and after the hair is wound into a curl formation around a rod or roller, the sulfur-to-sulfur cystine bonds are relinked or reestablished while the hair is in the curled formation by contacting the hair, in the new formation, with an oxidizing agent, such as hydrogen peroxide or a water-soluble bromate.

Waving lotions capable of breaking sulfur-to-sulfur cystine bonds in hair can include one or more reducing agents such as cysteine; cysteamine; acidic sodium hyposulfite; ammonium or sodium bisulfite; thioglycerol; thiolactic acid; thioglycolic acid or its salts, e.g., a thioglycolate, or a dithioglycolate; thiochloline or its salts; a monothioglycolic acid ester; N-acetylcysteamine; cysteamine; or combinations thereof. Examples of prior art reducing agents are disclosed in the following.

As set forth in U.S. Pat. No. 5,116,608, others have used a reducing agent composition that is a quaternary ammoniomercaptan, such as thiochloline, or its salts, together with a second reducing agent, such as thioglycolic acid, cysteamine or cysteine. Also, an N-acylcysteamine $HSCH_2CH_2NH—COR(R=2–10$ C alkyl), as a hair-reducing compound, has been used together with another reducing agent selected from the group consisting of cysteine, acidic sodium hyposulfite, sodium bisulfite, thioglycerol, and thiolactic acid, as disclosed in Japanese Pat. HEI 2-53714. Miyazaki et al. U.S. Pat. No. 4,139,610 discloses a combination of cysteine and N-acetylcysteine. This Assignee's Nandagiri et al. U.S. Pat. No. 5,260,054 discloses cysteamine as a reducing agent, and Showa Japanese Pat. 57062217 (Application No. 55-136857) discloses cysteamine together with an optional second reducing agent. U.S. Pat. No. 5,165,427 discloses cysteinamide as a reducing agent. U.S. Pat. No. 5,223,252 discloses a combination of a thioglycolate and cysteine at a pH of 7.5 to 9.5.

Kubo et al. U.S. Pat. No. 5,352,443) disclose the use of compounds capable of forming an alpha, beta unsaturated ketone-type structure for improving wave efficiency and reducing odor with thioglycolate ester waves. J. March, "Advance Organic Chemistry", John Wiley, N.Y., p. 1061 (1985) clearly states, and it is generally known to those skilled in the art, that poly-phenols with substitutions at the ortho and para positions are easily oxidized to the type of structure described by Kubo et al. by exposure to weak oxidizing agents, such as air. In fact, examples in Kubo et al. include only ortho and para substitutions. Those polyphenols which are meta substituted, such as those disclosed in this application, require much stronger oxidizing conditions in order to form such alpha, beta unsaturated ketone-type structures.

The reducing action of mercaptans on keratin is due mostly to the dissociated form of the thiol groups, the thiolate anion. "Acid" permanent waves sufficiently curl hair at a lower pH compared to alkaline permanent waves, because the waving agents in these permanent waves have low pKa values and thus exist predominantly in dissociated (thiolate) format a pH approaching neutral. Hence, the pKa value shows that some mercaptans are efficient at high pH while others with a low pKa value and high ionization constant are efficient at lower pH values. Therefore, it is generally understood, by those skilled in the art, that acceptable waving efficiency is usually obtained by working near the pKa of the active reducing agent. For example, it is well known that the alkaline salts of thioglycolic acid, e.g., the ammonium salt of thioglycolic acid (pKa=10.4) has acceptable waving efficiency only if the pH of solution exceeds 9, see Zviak, Charles, The Science of Hair Care, Permanent Waving and Hair Straightening, p. 191, 1986; while amides such as thioglycolamide (pKa=8.4), and esters such as glycerol thioglycolate (pKa=7.8) give acceptable waving efficiency at neutral.

Different reducing agents are effective to break the cystine bonds that cross-link human hair protein at different pHs. Generally speaking, the acid permanent wave compositions having lower pH values and include reducing agents such as bisulfites, e.g., ammonium bisulfite, or glycerol monothioglycolate, capable of breaking the sulfur-to-sulfur cystine bonds within lower pH ranges, whereas the alkaline permanent wave compositions, having pHs in the range of about 7.5 to 9.5, require an alkaline salt of thiglycolic acid so that the alkali can penetrate and swell the hair shaft for easier penetration of the reducing agent in order to break the sulfur-to-sulfur cystine bonds.

The use of diammonium dithiodiglycolate in acid or alkaline permanent wave lotions allows greater flexibility in processing time because it minimizes the possibility of overprocessing. This is due to the fact that the reaction of Ehioglycolic acid (TGA) with hair keratin is an equilibrium process. Thus, by including diammonium dithiodiglycolate (oxidized TGA) in the wave lotion, the rate of the reaction of the thioglycolic acid with hair keratin is decreased and the reaction prevented from going to completion.

Generally, the reducing agent lotion is applied to the hair by first shampooing the hair and then applying the reducing agent lotion to the hair, either before or after the hair is wrapped around suitable rollers. Once it is determined that the reducing agent has been in contact with the hair for a sufficient time period, the hair is rinsed thoroughly with water while still on the rollers or rods, and, while the hair remains on the rollers or rods, a neutralizing agent is applied to oxidize and reform the sulfur-to-sulfur bonds while the hair is in the new, rolled configuration. The neutralizing agent contains an oxidizing agent, such as hydrogen peroxide or a bromate salt, in order to reestablish the sulfur-to-sulfur bonds to leave the hair in a relatively permanent, e.g., 2–4 months, new configuration. The rods are removed before or after rinsing out the neutralizing agent.

When the reducing agent lotion is applied to sections of the head prior to rolling that portion of the hair onto the rods, it is called a lotion wrap, whereas when the hair is rolled on the rods or rollers first and then the lotion applied onto all of the hair after rolling, this is called a water wrap. The timing for the reducing agent to be in contact with the hair for a lotion wrap is begun from the time that all rods are on the head, and the timing for a water wrap begins from the time that the lotion application is completed. The capability of using a water wrap is clearly more desirable since the lotion is applied to the entire head of hair all at once in a short period of time and can be rinsed from the hair all at once to provide a more uniform reducing agent contact time for all of the hair.

It is well known in the art of hair permanent waving that the above-described reducing agents used in permanent waves to alter hair configuration result in a characteristic unpleasant odor in the hair. The intensity and duration of this unpleasant odor is formula dependent, depending, in particular, on the reducing agent used in the waving process. The conventional waving agents that are most widely used are ammonium thioglycolate, glycerol monothioglycolate (GMT), sodium or ammonium bisulfite, and cysteamine. All of these reducing agents leave residual odor on the hair after reaction with the hair that lasts from a day to one or two weeks. Some of the factors that play a role in the amount of odor left in the hair include the concentration and type of reducing agent, and the pH of the waving lotion. Some of the reducing agents are inherently more odoriferous than others. For example, it is widely known that cysteine hydrochloride is less odoriferous than GMT and the odor of sodium bisulfite is different and sometimes less objectionable than the mercaptans (thioglycolates).

The thiol reducing agents, such as ammonium thioglycolate, ammonium dithioglycolate, glyceryl monothioglycolate, and the like, produce malodor due to the formation of disulphides as shown below

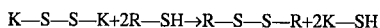
K—S—S—K+2R—SH→R—S—S—R+2K—SH

The reducing agent step of the permanent waving process forms cleaved disulfide (sulfide) hair sites, and other reaction products. The cleaved disulfide (cysteine) hair bonds having reactive sulfur sites are then oxidized to reestablish the hair bonds in the new hair configuration. Oxidation of the hair sulfur bonds present after reducing agent contact results in reestablished disulfide hair bonds, as well as other side reactions products that are odoriferous.

Post-perm odor has been cited by clients as one of the major drawbacks of permanent waving. Many attempts have been made by formulators to address this odor problem with only limited success. For example, in U.S. Pat. No. 5,223,252, Kolc, Abbott, and Nandagiri disclose a reducing agent composition including a combination of ammonium thioglycolate and cysteine-free base to reduce processing odor and post-perm odor while maintaining all other performance characteristics. In a Japanese patent application 3-271214, Segawa et al. disclose a post-perm treatment composition containing acids to reduce the odor of cysteamine waved hair.

Major marketers of permanent wave products in the United States have attempted to minimize the odor problem by using fragrances in the reducing agent-containing wave lotion and/or in the oxidizing agent-containing neutralizing composition.

While not being bound to any specific theory on the mechanism of action, it is theorized that one of the reasons why there is persistent post-perm odor is due to certain odoriferous residues formed by reaction of hair aldehydes with the reducing agent. It is theorized that these residues are left in the hair after the waving process as a result of being chemically bound to hair protein or as a result of the residues being trapped within the hair matrix. Malodor is given off from these residues when the hair is wetted. Over time, with repeated shampooing of the hair, these residues are released from the hair leaving the hair pleasant-smelling again.

Addressing this problem by simply fragrancing the hair, in an attempt to mask the unpleasant odor, is not effective since the masking fragrance is not long-lasting and does not prevent or reduce the formation of the odoriferous reaction products resulting from the reaction of newly formed hair aldehydes with reducing agent residue trapped in the hair. We have found that polyhydric phenols, particularly resorcinol and its derivatives, unexpectedly reduce the above-mentioned post-perm odors. It is theorized that the polyhydric phenols, used in accordance with the present invention, react with the hair aldehydes to prevent reaction between the reducing agent and hair aldehydes. Surprisingly, the polyhydric phenols are substantive to the hair so that the polyhydric phenols continue to react with newly formed hair aldehydes long after the permanent waving process is completed, even after repeated shampooing of the hair.

Sufficient polyhydric phenol remains substantive to the hair to continue reacting with newly formed hair aldehydes, thereby maintaining the hair essentially odor-free by preventing the newly formed hair aldehydes from reacting with any reducing agent that is trapped within the hair matrix. This odor-reducing potential is maximized when applied to the hair both before the waving lotion and after rinsing the neutralizer from the hair. Tests have shown the presence of the polyhydric polyol in hair after five shampoos, as set forth in Table VIII, infra.

The polyhydric polyols, such as resorcinol or resorcinol derivatives, contained in the compositions of the present invention are effective when applied to the hair at any of the above-described stages of the permanent waving process: (1) before contact with the waving lotion; (2) together with the waving lotion; (3) after contact with the waving lotion, and before rinsing; (4) after waving lotion contact and after rinsing, but before contacting the hair with the neutralizer (oxidizing agent-containing solution); (5) immediately after neutralization; and/or (6) long after neutralization; regardless of the particular reducing agent contained in the waving lotion. The compositions and methods of the present invention are particularly effective to prevent post-perm odor resulting from a cysteamine-containing permanent wave lotion, but also are effective to reduce odor resulting from contacting the hair with any other reducing agent that is reactive with hair aldehydes.

SUMMARY OF THE INVENTION

In brief, the present invention is directed to compositions and methods for reducing post perm odors by contacting the hair with a polyhydric phenol, particularly resorcinol or its derivatives, before, during, or after application of a reducing agent-containing waving lotion. The polyhydric phenol should have the following formula (I):

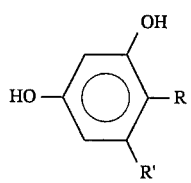

wherein
R'=H or OH,
R=H or $C_1$–$C_{12}$ alkyl,
  $C_1$–$C_{12}$ alcohol,
  $C_1$–$C_{12}$ aldehyde, or
a ketone having formula (II)

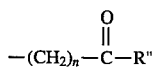

wherein
n=0–12, R"=$C_1$–$C_{12}$ alkyl, and wherein n+number of carbons in R"=1–12.

It has been found that hair aldehydes will react with the polyhydric phenols of formula (I), particularly resorcinol and its derivatives, at any position on the formula (I) ring that does not contain an OH radical, to substantially reduce post perm odors.

Accordingly, one aspect of the present invention is to provide a composition and method for reducing post-perm odors resulting from the action of a permanent wave reducing agent on hair.

Another aspect of the present invention is to provide a composition and method for minimizing post-perm odors by reacting hair aldehydes with polyhydric phenols, particularly resorcinol and resorcinol derivatives.

Yet another aspect of the present invention is to provide a composition and method for reducing post-perm odors associated with contacting hair with a reducing agent in a waving lotion during the permanent wave process by contacting the hair with a polyhydric phenol, such as resorcinol, thereby reacting the hair aldehydes to the hair aldehydes from reacting with the waving lotion reducing agent. The polyhydric phenols are particularly effective to reduce post-perm odors resulting from the use of a cysteamine reducing agent, but also are effective against post-perm odors caused by other reducing agents, such as glycerol monothioglyolates (GMT), ammonium thioglycolates (ATG), and any other reducing agent that is reactive with hair aldehydes.

The above and other aspects and advantages of the present invention will become more apparent from the following detailed description of the preferred embodiments.

DETAILED DESCRIPTION OF THE PREFERRED EMBODIMENTS

In accordance with the present invention, reducing post-perm odor is achieved by contacting the hair before, during, or after the permanent waving process, with a composition containing a polyhydric phenol having a general formula (I):

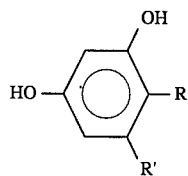

wherein

R'=H or OH,
R=H or $C_1$–$C_{12}$ alkyl,
  $C_1$–$C_{12}$ alcohol,
  $C_1$–$C_{12}$ aldehyde, or
a ketone having formula (II)

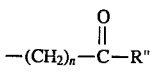

wherein
n=0–12, R"=$C_1$–$C_{12}$ alkyl, and wherein n+number of carbons in R"=1–12.

Specific examples of polyhydric phenol compounds of formula (I) include resorcinol;

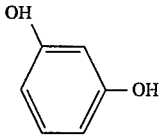

hexyl resorcinol:

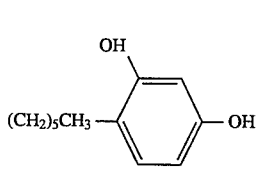

acetaldehyde resorcinol:

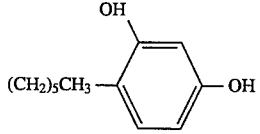

catechol:

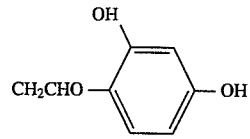

pyrogallol:

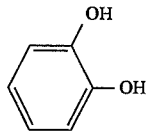

phloroglucinol:

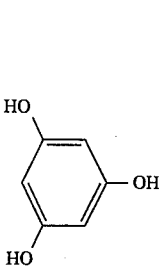

4-chlororesorcinol:

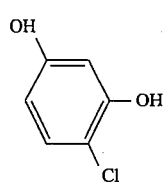

and the like.

The polyhydric polyol should be present in the post-perm odor-reducing composition in an amount in the range of about 0.05% to about 10% by weight of the composition. In a concentration below about 0.05% by weight, the odor-reducing property is insufficient, since insufficient polyhydric polyol is available for continued reaction with hair aldehydes. Above about 10% by weight polyhydric polyol in the post-perm odor-reducing composition, the scalp and/or skin may become irritated. The preferred concentration of polyhydric phenol is in the range of about 0.1% to about 5% by weight, with the most preferred concentration in the range of about 1% to about 5% by weight. A polyhydric polyol concentration of about 2% by weight appears to have the least deleterious effect on wave efficiency. However, when the polyhydric polyol is included in an amount greater than about 2% by weight, the reducing agent concentration can be increased to achieve wave efficiency, while essentially eliminating post-perm odor.

The pH of the polyhydric polyol composition should be in the range of about 1.5 to about 10. Below a pH of about 1.5, the composition may irritate the scalp and/or skin. Above a pH of about 10, the composition may become unstable. The preferred pH for the polyhydric polyol-containing post-perm odor-reducing composition is in the range of about 1.5 to about 8.5, with the most preferred pH being in the range of about 3.5 to about 7.0.

The post-perm odor reducing composition containing one or more of the above-described polyhydric polyols can be in the form of a solution of the polyhydric polyol in water; or, for post-perm use, can be in the form of a shampoo or conditioner; or a 2 in 1 shampoo and conditioner. In one embodiment, the composition can be thickened, e.g., to a viscosity in the range of about 1000 centipoises to about 5000 centipoises (spindle 4, 20 RPM), as desirable for use as hair relaxer and spritz formulations.

The following Examples 1–3 detail compositions containing resorcinol-containing compositions at various pH values and various resorcinol concentrations, without being thickened, wherein the ingredients are added in the order shown.

EXAMPLE 1

| 1% resorcinol; pH = 8.5 | | | |
|---|---|---|---|
| No. | Ingredient | Weight (g) | Weight % |
| 1. | Water, Deionized | 98.0 | 89.0 |
| 2. | Resorcinol | 1.0 | 1.0 |
| 3. | Sodium Hydroxide, 0.1N | QS | QS |

EXAMPLE 2

| 2% Resorcinol; pH = 7.0 | | | |
|---|---|---|---|
| Item | Ingredient | Weight % | Weight (g) |
| 1. | Water, Deionized | 97.99 | 2939.8 |
| 2. | Sodium Hydroxide, 50% (liq) | 0.07 | 0.2 |
| 3. | Resorcinol | 2.00 | 60.0 |

EXAMPLE 3

| 4% resorcinol; pH = 8.5 | | | |
|---|---|---|---|
| No. | Ingredient | Weight (g) | Weight % |
| 1. | Water, Deionized | 95.64 | 95.64 |
| 2. | Resorcinol | 4.00 | 4.00 |
| 3. | Sodium Hydroxide, 50% | 0.36 | 0.36 |

EXAMPLE 4

| 8% resorcinol; pH = 8.5 | | | |
|---|---|---|---|
| No. | Ingredient | Weight (g) | Weight % |
| 1. | Water, Deionized | 91.20 | 91.20 |
| 2. | Resorcinol | 8.0 | 8.0 |
| 3. | Sodium Hydroxide, 50% | 0.80 | 0.80 |

EXAMPLE 5

| 9.23% resorcinol; pH = 8.5 | | | |
|---|---|---|---|
| No. | Ingredient | Weight (g) | Weight % |
| 1. | Water, Deionized | 98.0 | 89.0 |
| 2. | Resorcinol | 0.56 | 9.23 |
| 3. | Sodium Hydroxide, 0.1N | 0.64 | 10.54 |

When provided in the form of a shampoo composition, the composition should include about 1% to about 65% by weight of an anionic, cationic, and/or amphoteric surfactant, preferably about 5% to about 20% by weight of an anionic cleansing surfactant, e.g., sodium lauryl sulfate, such as disclosed in Duvel, U.S. Pat. No. 5,034,218, hereby incorporated by reference. One or more additional components, such as conditioning agent, e.g., a silicone gum and/or a silicone oil, also may be included in the shampoo formulation, if desired, as disclosed in the Duvel '218 patent. Also, the composition can be provided in the form of a hair conditioning composition by including one or more hair conditioning agents together with the polyhydric phenol and water composition, such as the conditioning agent disclosed in the Noe, U.S. Pat. No. 4,976,956, hereby incorporated by reference. The conditioning agent can be included in an amount of about 0.1% to about 20% by weight of the composition. When provided in the form of a reducing agent-containing waving lotion, the composition can include a hair-reducing agent, such as cysteamine, in an amount of about 0.5% to about 20% by weight, preferably about 1% to about 15% by weight reducing agent, and may include additional waving lotion components, as disclosed in Nandagiri, et al., U.S. Pat. No. 5,382,426, hereby incorporated by reference.

The following Examples 6 and 7 are resorcinol-containing compositions that include a cysteamine reducing agent for use as a waving lotion.

EXAMPLE 6

| | 10% resorcinol; pH = 8.3 | | |
|---|---|---|---|
| No. | Ingredient | Weight (g) | Weight % |
| 1. | Water, Deionized | 14.42 | 72.10 |
| 2. | Cysteamine.HCl, 75% (aq) | 2.75 | 13.75 |
| 3. | Resorcinol | 2.00 | 10.00 |
| 4. | Sodium Hydroxide, 50% | 0.83 | 4.15 |

EXAMPLE 7

| | 10% resorcinol; pH = 8.3 | | |
|---|---|---|---|
| No. | Ingredient | Weight (g) | Weight % |
| 1. | Water, Deionized | 13.62 | 68.10 |
| 2. | Cysteamine.HCl 75% (aq) | 2.75 | 13.75 |
| 3. | Resorcinol | 2.00 | 10.00 |
| 4. | Sodium Hydroxide, 50% | 0.83 | 4.15 |
| 5. | PEG-15 Nonyl Phenyl Ether (Igepal) | 0.625 | 3.13 |
| 6. | Fragrance | 0.175 | 0.88 |

The following Example 8 is a shampoo composition containing resorcinol and a surfactant (sodium lauryl sulfate) for use as a shampoo/post-perm odor reducer.

EXAMPLE 8

| 2% resorcinol; pH = 4.5 | | |
|---|---|---|
| Ingredient | Weight (g) | Weight % |
| Water, Deionized | 83.0 | 83.0 |
| SLS (sodium lauryl sulfate) | 15.0 | 15.0 |
| Resorcinol | 2.0 | 2.0 |

The following Examples 9–12 are thickened resorcinol-containing compositions at various resorcinol concentrations; viscosities; and pH values which can be used either as pre-, mid- or post treatments.

EXAMPLE 9

| | 2% Resorcinol; 2100 cps.; pH = 3.5 | | |
|---|---|---|---|
| Item | Ingredient | Weight % | Weight (g) |
| 1. | Water, Deionized | 2807.61 | 93.587 |
| 2. | Natrosol (gum) | 12.00 | 0.400 |
| 3. | Glycerol USP | 6.00 | 0.200 |
| 4. | Ajidew N-50 (humectant) | 6.00 | 0.200 |
| 5. | PEG-15 Nonyl Phenyl Ether | 63.00 | 2.100 |
| 6. | Fragrance 6301-AT | 21.00 | 0.700 |
| 7. | Citric Acid, 50% (liq) | 4.79 | 0.160 |
| 8 | Disodium EDTA | 3.00 | 0.100 |
| 9. | Sodium Hydroxide, 50% (liq) | 0.10 | 0.003 |
| 10. | Ethoquad 0/12-PG | 9.00 | 0.300 |
| 11. | Resorcinol | 60.00 | 2.000 |
| 12. | DMDM Hydantoin | 7.50 | 0.250 |

Initial Viscosity 2100 cps (spindle 4/20 RPM)
Manufacturing Instructions:
1. Add agents in order until Igepal (fragrance solubilizer).
2. Igepal should be clear when solubilizing fragrance.
3. Resorcinol is added at the end and DI water, citric acidare QS to desired pH.

EXAMPLE 10

| | 2% Resorcinol; 2300 cps.; pH = 3.5 | | |
|---|---|---|---|
| Item | Ingredient | Weight % | Weight (g) |
| 1. | Water, Deionized | 2812.40 | 93.747 |
| 2. | Natrosol (gum) | 12.00 | 0.400 |
| 3. | Glycerol USP | 6.00 | 0.200 |
| 4. | Ajidew N-50 (humectant) | 6.00 | 0.200 |
| 5. | PEG-15 Nonyl Phenyl Ether | 63.00 | 2.100 |
| 6. | Fragrance 6301-AT | 21.00 | 0.700 |
| 7. | Citric Acid, 50% (liq) | 7.000 | 0.230 |
| 8 | Disodium EDTA | 3.00 | 0.100 |
| 9. | Sodium Hydroxide, 50% (liq) | 0.10 | 0.003 |
| 10. | Ethoquad 0/12-PG | 9.00 | 0.300 |
| 11. | Resorcinol | 60.00 | 2.000 |

Initial Viscosity 2300 cps (spindle 4/20 RPM)
Manufacturing Instructions:
1. Add agents in order until Igepal. (5)
2. Igepal should be clear when solubilizing fragrance.
3. Resorcinol is added at the end and DI water, NaOH are QS to desired pH.

EXAMPLE 11

| | 2% Resorcinol; 1100 cps.; pH = 7.0 | | |
|---|---|---|---|
| Item | Ingredient | Weight % | Weight (g) |
| 1. | Water, Deionized | 2815.65 | 93.855 |
| 2. | Natrosol (gum) | 12.00 | 0.400 |
| 3. | Glycerol USP | 6.00 | 0.200 |
| 4. | Ajidew N-50 (humectant) | 6.00 | 0.200 |
| 5. | PEG-15 Nonyl Phenyl Ether | 63.00 | 2.100 |
| 6. | Fragrance 6301-AT | 21.00 | 0.700 |
| 7. | Citric Acid, 50% (liq) | 1.92 | 0.064 |
| 8 | Disodium EDTA | 3.00 | 0.100 |
| 9. | Sodium Hydroxide, 50% (liq) | 2.43 | 0.081 |
| 10. | Ethoquad 0/12-PG | 9.00 | 0.300 |
| 11. | Resorcinol | 60.00 | 2.000 |

Initial Viscosity 1100 cps (spindle 4/20 RPM)
Manufacturing Instructions:
1. Add agents in order until Igepal.
2. Igepal should be clear when solubilizing fragrance.
3. Resorcinol is added at the end and DI water, NaOH are QS to desired pH.

EXAMPLE 12

| | 2% Resorcinol; 1100 cps.; pH = 3.0 | | |
|---|---|---|---|
| Item | Ingredient | Weight % | Weight (g) |
| 1. | Water, Deionized | 2811.10 | 93.700 |
| 2. | Natrosol (gum) | 12.00 | 0.400 |
| 3. | Glycerol USP | 6.00 | 0.200 |
| 4. | Ajidew N-50 (humectant) | 6.00 | 0.200 |
| 5. | PEG-15 Nonyl Phenyl Ether | 63.00 | 2.100 |
| 6. | Fragrance 6301-AT | 21.00 | 0.700 |
| 7. | Citric Acid, 50% (liq) | 0.10 | 0.003 |
| 8 | Disodium EDTA | 3.00 | 0.100 |
| 9. | Sodium Hydroxide, 50% (liq) | 1.30 | 0.043 |
| 10. | Ethoquad 0/12-PG | 9.00 | 0.300 |
| 11. | Resorcinol | 60.00 | 2.000 |
| 12. | DMDM Hydantoin | 7.50 | 0.250 |

Initial Viscosity 1100 cps (spindle 4/20 RPM)
Manufacturing Instructions:
1. Add agents in order until Igepal.
2. Igepal should be clear when solubilizing fragrance.
3. Resorcinol is added at the end and DI water, NaOH are QS to desired pH.

Odor intensity experiments were performed with resorcinol as an odor suppressant for cysteamine-based waving lotion perms at various steps in the perm process:

(a) prewrap—before contacting the hair with the cysteamine reducing solution (Pre-Perm);

(b) in the reducing solution (Co-Treat)—note that when the resorcinol is used with the reducing solution, preferably the resorcinol is added before use, if mixed during manufacture stability may be effected;

(c) between the reducing solution and the neutralizer (Midstep); and (d) after neutralization—can be much later (Post Treatment).

The waving lotion composition used in the odor intensity experiments were as follows:

| First Cysteamine-Based Wave Lotion Formulation for Resorcinol Studies, pH 8.3 | | |
|---|---|---|
| Ingredient | Weight (g) | Weight % |
| Water, Deionized | 82.70 | 82.70 |
| Cysteamine.HCl, 75% aq. | 11.00 | 11.00 |
| PEG-15 Nonyl Phenyl Ether | 2.10 | 2.10 |
| Ammonium Hydroxide, 28% | 2.20 | 2.20 |
| Ammonium Bicarbonate | 2.00 | 2.00 |

| Second Cysteamine-Based Wave lation Formulation for Resorcinol Studies, pH 8.5 | | |
|---|---|---|
| Ingredient | Weight (g) | Weight % |
| Water, Deionized | 79.50 | 79.50 |
| Cysteamine.HCl, 75% aq. | 13.00 | 13.00 |
| PEG-15 Nonyl Phenyl Ether | 2.10 | 2.10 |
| Ammonium Hydroxide, 28% | 2.40 | 2.40 |
| Ammonium Bicarbonate | 2.00 | 2.00 |

Neutralizers used with the above first and second cysteamine-based waving lotions, to complete the perms, are hydrogen peroxide-based.

| GMT-Based Waving Lotion Used In Conjunction With Resorcinol Studies | | |
|---|---|---|
| Ingredient | Weight (g) | Weight % |
| Water, Deionized | 81.62 | 81.62 |
| Sodium Borate | 1.00 | 1.00 |
| DMDM Hydantoin | 0.25 | 0.25 |
| Ammonium Thioglycolate, 60% | 3.33 | 3.33 |
| Diammonium Dithioglycolate, 40% | 7.20 | 7.20 |
| Polyquaternium-10 | 0.10 | 0.10 |
| Polysorbate-20 | 2.00 | 2.00 |
| Ammonium Hydroxide, 28 % | 4.50 | 4.50 |

79.6 g of this base is then mixed with 24 g of activator (glycerol monothioglycolate) for a final pH of about 8.0.

| MEATG/Cysteamine Hybrid Formulation, pH 7.00 Used In Conjunction With Resorcinol Studies | | |
|---|---|---|
| Ingredient | Weight (g) | Weight % |
| Water, Deionized | 65.41 | 65.41 |
| Tetrasodium EDTA | 0.51 | 0.51 |
| Sodium Dihydrogen Phosphate | 2.50 | 2.50 |
| Cysteamine.HCl, 75% (aq) | 11.00 | 11.00 |
| MEA Thioglycolate, 40% | 16.81 | 16.81 |
| Monoethanolamine | 1.27 | 1.27 |
| PEG-15 Nonyl Phenyl Ether | 2.50 | 2.50 |

| Finesse Extra Body Conditioner Ingredients List Used In Conjunction with Resorcinol | |
|---|---|
| INGREDIENTS | |
| Soft Water | Disodium EDTA |
| Liquid Citric Acid, 50% | Methylchloroisothiazolinone |
| Stearamidopropyl Dimethylamine | Methylisothiazolinone |
| Propylene Glycol | DMDM Hydantoin |
| Dicetyldimonium Chloride/PG | Potassium Hydroxide, Liquid 50% |
| Cetearyl Alcohol and Ceteareth-20 | Cyclomethicone |
| Cetyl Alcohol | Dimethicone |
| DL-Panthenol | Fragrance |
| Potassium Chloride | |

| Pantene Extra Body Conditioner Ingredients List Used In Conjunction With Resorcinol | |
|---|---|
| INGREDIENTS | |
| Soft Water | Hydroxyethylcellulose |
| Cyclomethicone | Stearamidopropyl Dimethylamine |
| Cetyl Alcohol | Ceteareth-20 |
| Dimethicone | Glyceryl Stearate |
| Quaternium-18 or Quaternary Ammonium Compounds, Bis (Hydrogenated Tallow Alkyl) Dimethyl, chlorides | Fragrance |
| Panthenol | Citric Acid |
| Panthenyl Ethyl Ether | Dimethicone Copolyol |
| Phytantriol | Methylchloroiosothiazolinone |
| Pantethine | Methylisothiazolinone |
| Stearyl Alcohol | |

The waving lotions used in the permanent waving process for collection of the data of FIGS. 1–3 were either the first cysteamine-based waving lotion, or the second cysteamine-based waving lotion. As shown in FIGS. 1–3, the midstep treatment at about 0.5% to about 2% resorcinol was most effective in reducing post perm odor. Resorcinol was also included in shampoo and conditioner bases and also reduced the glycerol monothioglycolate (GMT) odor from GMT-based waving lotions. A summary of the odor intensity results for resorcinol, hexylresorcinol, and acetaldehyderesorcinol is shown in Table I.

TABLE I

| CATE-GORY | RE-SPONSE | PARAMETERS | RESULTS |
|---|---|---|---|
| Midstep | Odor Intensity | 0.1 to 4% concentration of Resorcinol, pH 8.5 first cysteamine-based waving lotion | 2%, 4% most effective. No detectable odor. |
| Midstep | Odor Intensity | 0.1 to 2% concentration of Resorcinol, pH 8.5 first cysteamine-based waving lotion | 2% most effective. No detectable odor. |
| Post-Perm | Odor Intensity | 0.1 to 2% concentration of Resorcinol, pH 8.5 first cysteamine-based waving lotion | 2% most effective. No detectable odor. |
| Pre-Perm | Odor Intensity | 0.1 to 2% concentration of Resorcinol, pH 8.5 first cysteamine-based waving lotion | 2% most effective. No detectable odor. |
| Midstep | Odor Intensity | 2% Resorcinol, pH 3.5 GMT-based waving lotion, Design; Control: second cysteamine-based waving lotion | Resorcinol could have distinct advantage with GMT waves such as Extra Body. |
| Co-Treat | Odor Intensity | First cysteamime-based waving lotion with 0.73M Resorcinol co-treatment, pH 8.5 (8% solution) | Odor was prevented with Resorcinol in the wave. |
| Midstep | Odor Intensity | First cysteamine-based waving lotion with 0.8M Resorcinol Midstep treatment, pH 8.5 (9% solution) | Odor did not occur after midstep treatment. |
| Post-Perm | Odor Intensity | First cysteamime-based waving lotion with 0.8M Resorcinol Post-treatment, pH 8.5 | Odor was removed with the post-perm odor treatment. |
| Wash-out | Odor Intensity | First cysteamine-based waving lotion with 0.73M, 0.1M Resorcinol, Midstep and Post-Perm treatment, pH 8.5 (8%, 0.1% solution) | Washout over one week did not rebloom the odor. |
| Midstep Post-Perm | Odor Intensity | Second cysteamine-based waving lotion with 1% Resorcinol (R), pH 8.5 Hexylresorcinol (H), Acetaldehyde Resorcinaldehyde (A) additions | No odor on various treatment combinations. Resorcinol Best. R > H > A |
| Pre-Perm Wash-out | Odor Intensity | Second cysteamine-based waving lotion with 0.73M, 0.09M Resorcinol pH 8.5 (8%, 0.1% solutions) | No odor on initial and after wash and 2 day incubation. |
| Post-Perm | Odor Intensity | 2% Resorcinol in sodium lauryl sulfate (SLS) base and Finesse Extra Body base, unfranganced GMT-based waving lotion plus Resorcinol | Shampoo seems best place for resorcinol by panelist choice. GMT based waving lotion plus |

TABLE I-continued

| CATE-GORY | RE-SPONSE | PARAMETERS | RESULTS |
|---|---|---|---|
| Post-Perm | Odor Intensity | 2% Resorcinol in sodium lauryl sulfate (SLS) base and Finesse Extra Body Conditioner and Spritz base, unfragranced | resorcinol lowered GMT odor. Works to prevent odor when placed in shampoo, conditioner and spritz bases. |

Also, different types of perms were used for waving efficiency experiments on tresses:

(a) first and second cysteamine-based waving lotions, at approximately 8.3 wt. % cysteamine cysteamine HCl, pH 8.4 and 9.75 wt. % cysteamine HCl, pH 8.5, respectively; and (b) GMT-based waving lotion.

The resorcinol-containing compositions used in the waving efficiency experiments on tresses all contained 2% by weight resorcinol and had a pH of 3.5, as follows:

EXAMPLE 13

2% Resorcinol; pH = 3.5

| Item | Ingredient | Weight % | 500 g | Actual |
|---|---|---|---|---|
| 1 | Water, Deionized | 94.26 | 471.29 | 471.29* |
| 2 | Glycerol USP | 0.2 | 1.00 | 1.00 |
| 3 | Ajidew N-50 (humectant) | 0.2 | 1.00 | 1.00 |
| 4 | PEG-15 Nonyl Phenyl Ether | 2.1 | 10.50 | 10.50 |
| 5 | Fragrance 6301-AT | 0.7 | 3.50 | 3.50 |
| 6 | Disodium EDTA | 0.1 | 0.50 | 0.50 |
| 7 | Ethoquad 0/12-PG | 0.3 | 1.50 | 1.50 |
| 8 | Resorcinol | 2.0 | 10.00 | 10.00 |
| 9 | Citric Acid | 0.14 | 0.71 | 0.71 |

The resorcinol-containing compositions were tested when used as a pre-perm, co-treat, mid-step and post-perm composition to determine their effect on wave efficiency. The results are shown in Table II, as well as a final experiment relating to stability.

TABLE II

| CATE-GORY | RE-SPONSE | PARAMETERS | RESULTS |
|---|---|---|---|
| Midstep and Co-Treat | Wave Efficiency | First cysteamine-based waving lotion with 1%, 8% Resorcinol midstep, pH 8.5; and 8% in the wave lotion | 1% Midstep could help increase wave efficiency. Resorcinol can be placed into wave right before usage. |
| Midstep | Wave Efficiency | Second cysteamine-based waving lotion with 2% and 4% Resorcinol midstep, pH 8.5 | 2% produces best results relative to waving efficiency. |
| Pre-Perm | Wave Efficiency | First cysteamine-based waving lotion with 2% Resorcinol thick prewrap, (Example 9) pH 3.5 | Prewrap helps increase wave efficiency of first cysteamine-based waving lotion |
| Stability | Stability | 2% Resorcinol in thick, thin, unpreserved and preserved base at | pH 3.5 samples fairing better than pH 7.0 at one week and one |

TABLE II-continued

| CATE-GORY | RE-SPONSE | PARAMETERS | RESULTS |
|---|---|---|---|
| | | pH 3.5 and 7.0 | month. Clear in opaque LDPE. Preservatives can be utilized. |

BRIEF DESCRIPTION OF THE DRAWINGS

Permanent waves were performed on six hair tresses using the first cysteamine-based waving lotion, as well as a glycerol monothioglycolate-based waving lotion (GMT-based) with and without contacting the hair with a resorcinol-containing composition (1) prior to contacting the hair with the cysteamine-based waving lotion (pre-treatment); (2) after cysteamine-based waving lotion contact and after rinsing (midstep); and (3) after neutralization of the waving lotion with a hydrogen peroxide-based neutralizer (post-perm treatment) to determine the odor-reducing effects of resorcinol on a cysteamine-based waving lotion, at various concentrations of resorcinol between 0.1% and 2.0% by weight. A six-person panel trained to detect post-perm odors then sniffed the hair tresses and rated the post-perm odor on a scale of 1.0 to 6.0–6.0 representing a stronger odor detected, and 1.0 representing a weaker post-post perm odor. The results for pre-treatment are shown in FIG. 1; for midstep in FIG. 2; and for post-perm treatment in FIG. 3.

The resorcinol-containing compositions used in collecting the data for FIGS. 1–3 were as follows:

| 0.1–2% Resorcinol; pH - 8.5 | | |
|---|---|---|
| INGREDIENT | WEIGHT (g) | WEIGHT (%) |
| 1. DI Water | 99.90 | 99.90 |
| 2. Resorcinol | 0.10 | 0.10 |

| 0.1–2% Resorcinol; pH - 8.5 | | |
|---|---|---|
| INGREDIENT | WEIGHT (g) | WEIGHT (%) |
| (No pH adjustment necessary) | | |
| 1. DI Water | 99.47 | 99.47 |
| 2. Resorcinol | 0.50 | 0.50 |
| 3. Sodium Hydroxide, 50% | 0.03 | 0.03 |

| 0.1–2% Resorcinol; pH - 8.5 | | |
|---|---|---|
| INGREDIENT | WEIGHT (g) | WEIGHT (%) |
| 1. DI Water | 98.90 | 98.90 |
| 2. Resorcinol | 1.00 | 1.00 |
| 3. Sodium Hydroxide, 50% | 0.10 | 0.10 |
| 1. DI Water | 97.83 | 97.83 |
| 2. Resorcinol | 2.00 | 2.00 |
| 3. Sodium Hydroxide, 50% | 0.17 | 0.17 |

Figure 1:
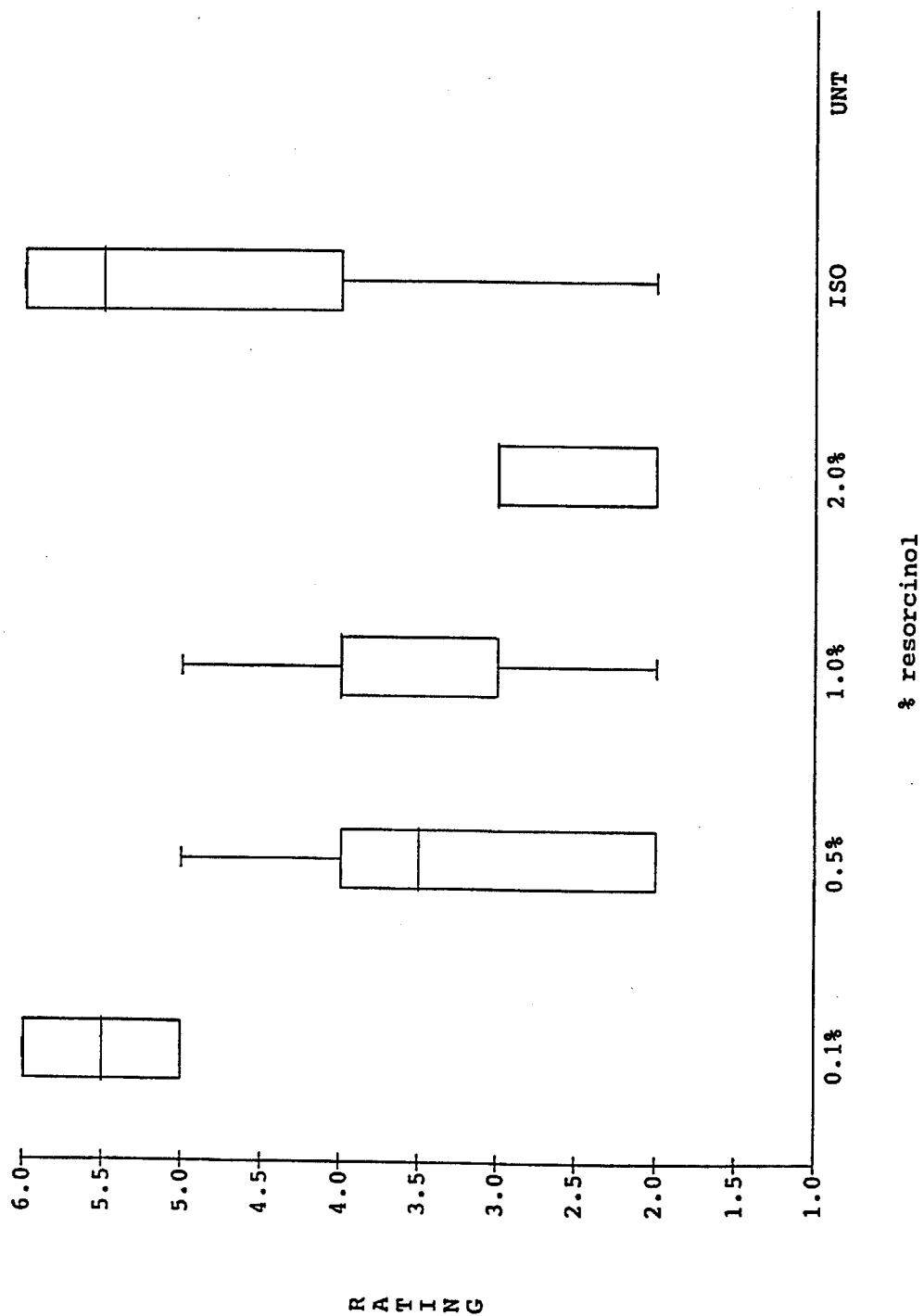
Figure 2:
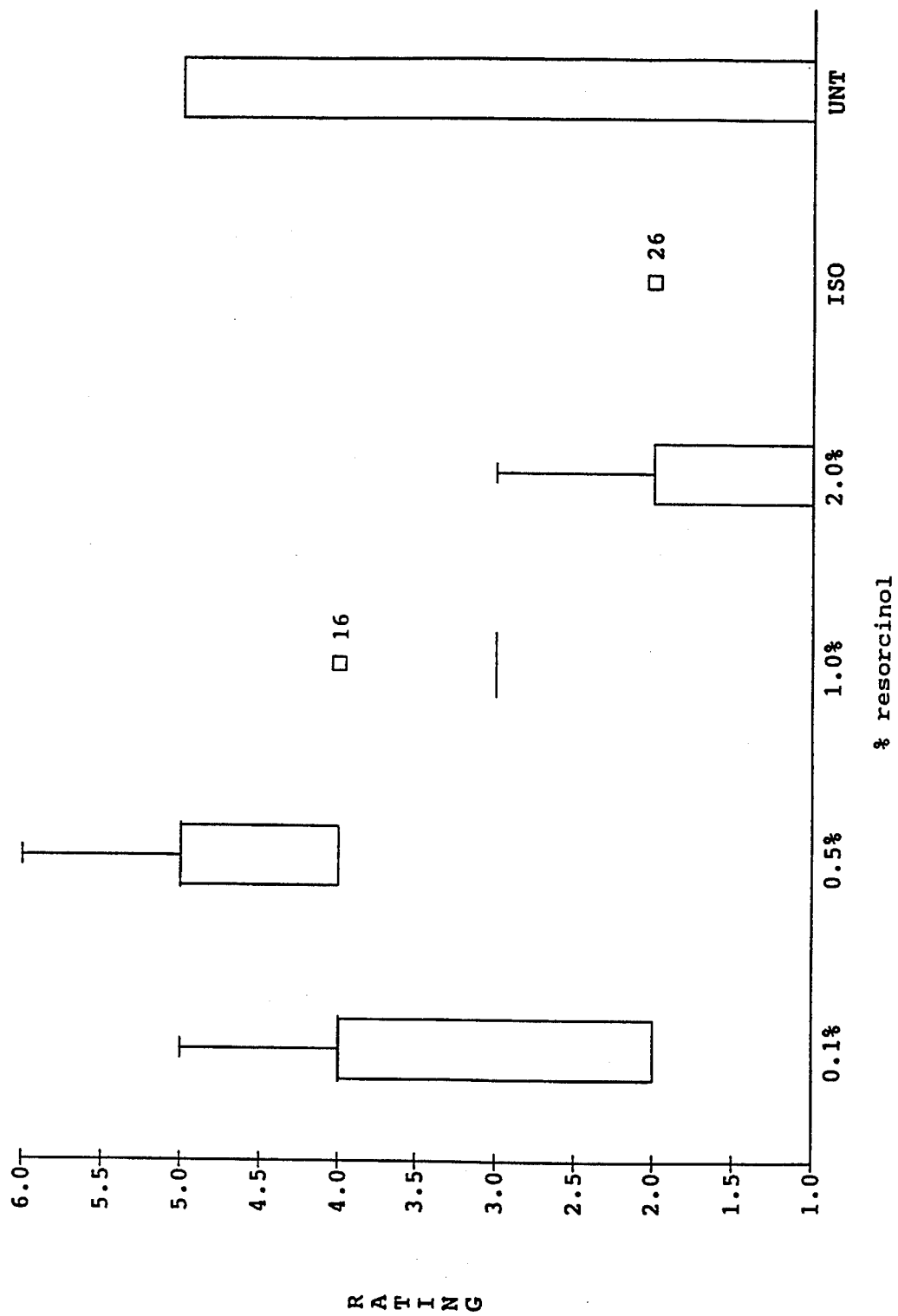
Figure 3:
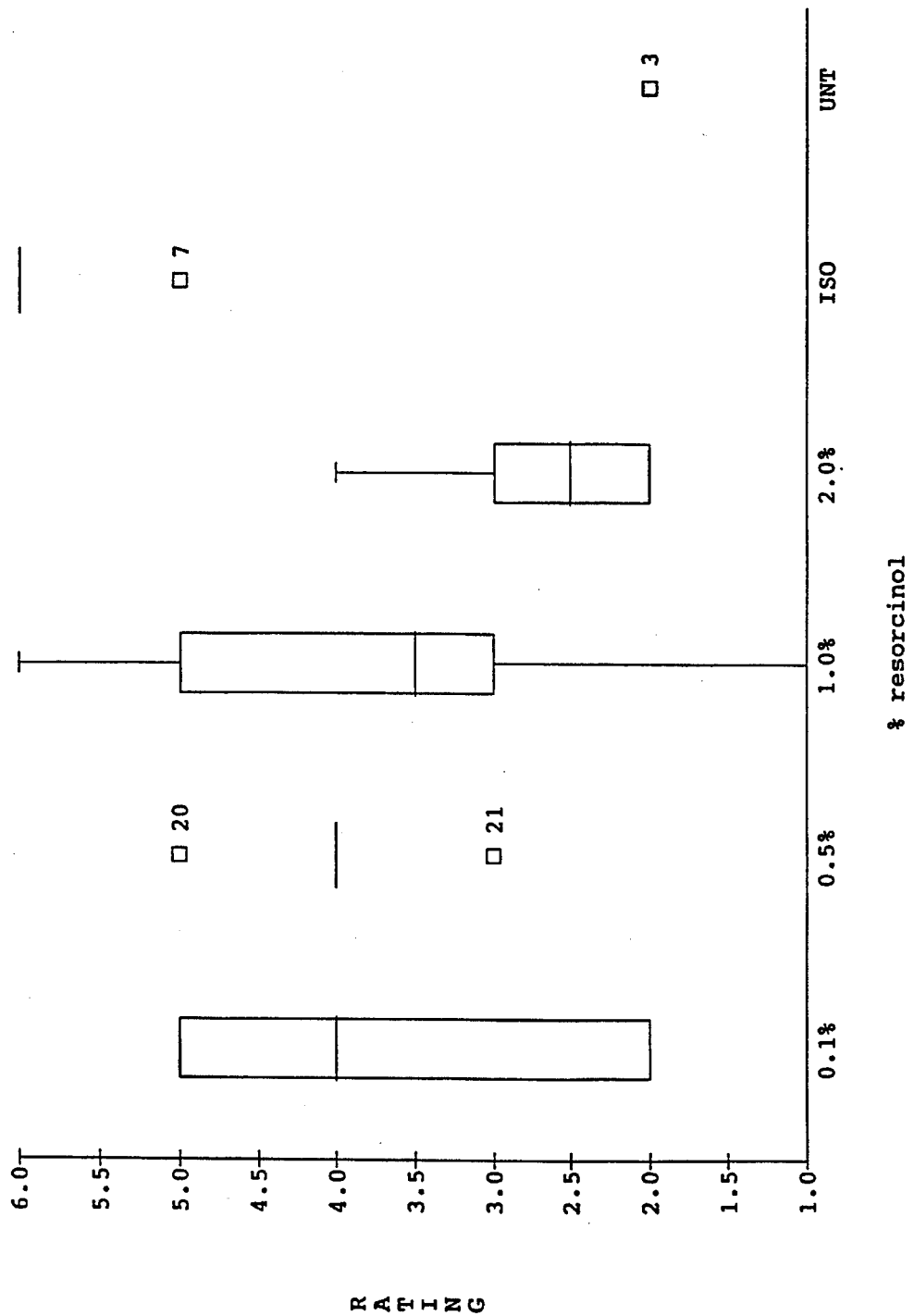
Figure 4:
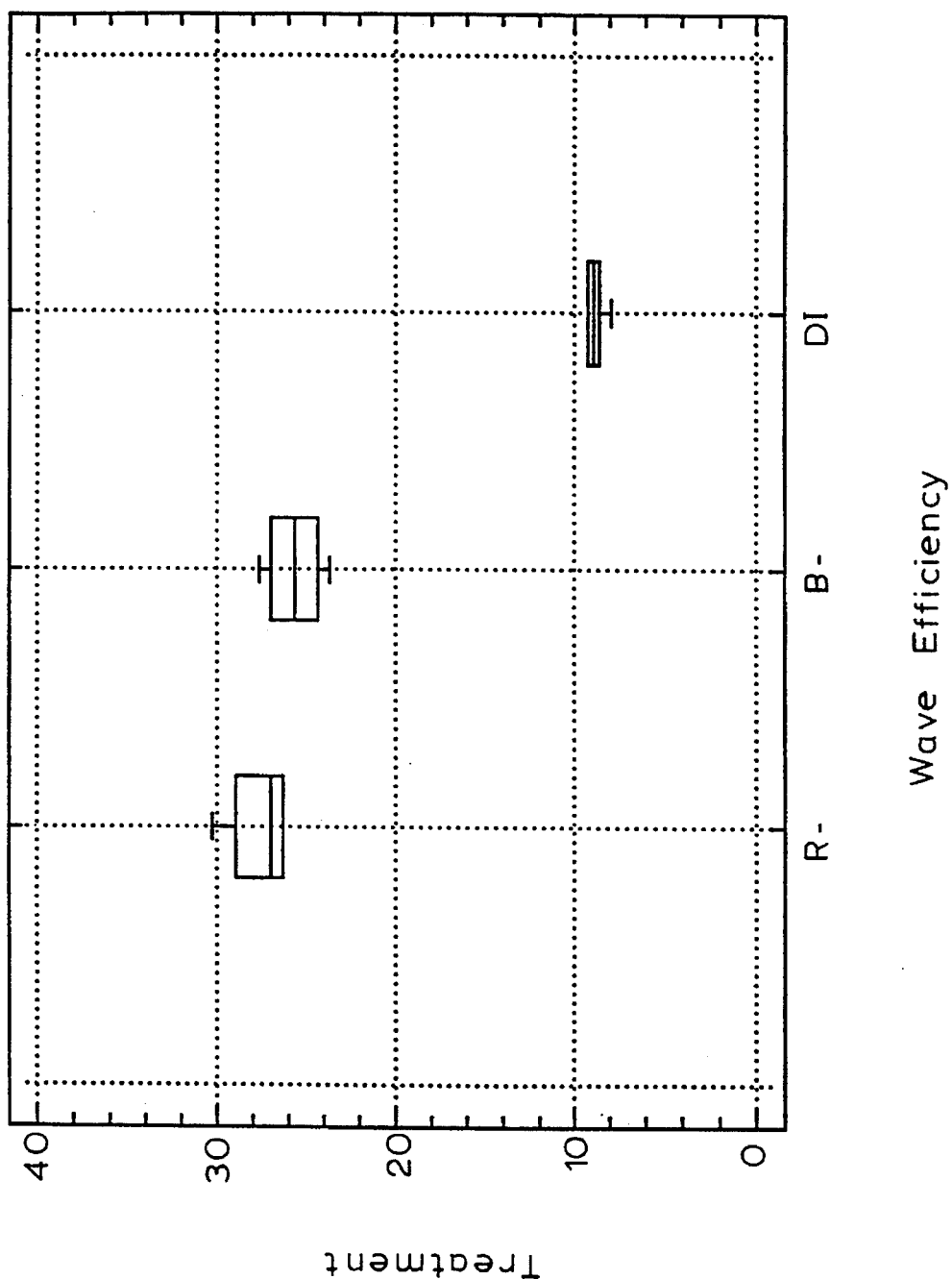

The waving efficiencies for cysteamine waves with a 2% resorcinol (R-cysteamine) and a 0.25% benzaldehyde (B-cysteamine) prewrap are compared with that of deionized water (DI) in FIG. 4 which was constructed from the data in Table III. The composition of the 2% resorcinol prewrap is shown in the fourth (last) example in the table above. The benzaldehyde prewrap is a commercial product.

The resorcinol-containing cysteamine-based composition (R-cysteamine) of Example 13 was compared to deionized water (DI) and a benzaldehyde-containing composition (B-cysteamine) containing 0.25% by weight benzaldehyde, for wave efficiency when applied as a pre-treatment (prior to contact with the cysteamine reducing agent). The results of the wave efficiency experiments are shown in FIG. 4 and constructed from the date of Table III:

TABLE III

| Sample Name | Tress 1 Length (cm) | Wave Efficiency (%) | Tress 2 Length (cm) | Wave Efficiency (%) | Tress 3 Length (cm) | Wave Efficiency (%) | Tress 4 Length (cm) | Wave Efficiency (%) | Tress 5 Length (cm) | Wave Efficiency (%) | Tress 6 Length (cm) | Wave Efficiency (%) | Average Tress Length (cm) | Average Wave Efficiency (%) |
|---|---|---|---|---|---|---|---|---|---|---|---|---|---|---|
| R-cysteamine | 11.1 | 27.0 | 10.8 | 28.9 | 11.2 | 26.3 | 11.1 | 27.0 | 11.2 | 26.3 | 10.6 | 30.3 | 11.0 | 27.6 |
| B-cysteamine | 11.6 | 23.7 | 11.5 | 24.3 | 11.4 | 25.0 | 11.0 | 27.6 | 11.1 | 27.0 | 11.2 | 26.3 | 11.3 | 26.3 |
| DI | 13.8 | 9.2 | 13.9 | 8.6 | 13.8 | 9.2 | 13.9 | 8.6 | 14.0 | 7.9 | 13.8 | 9.2 | 13.9 | 8.8 |

Figure 5:
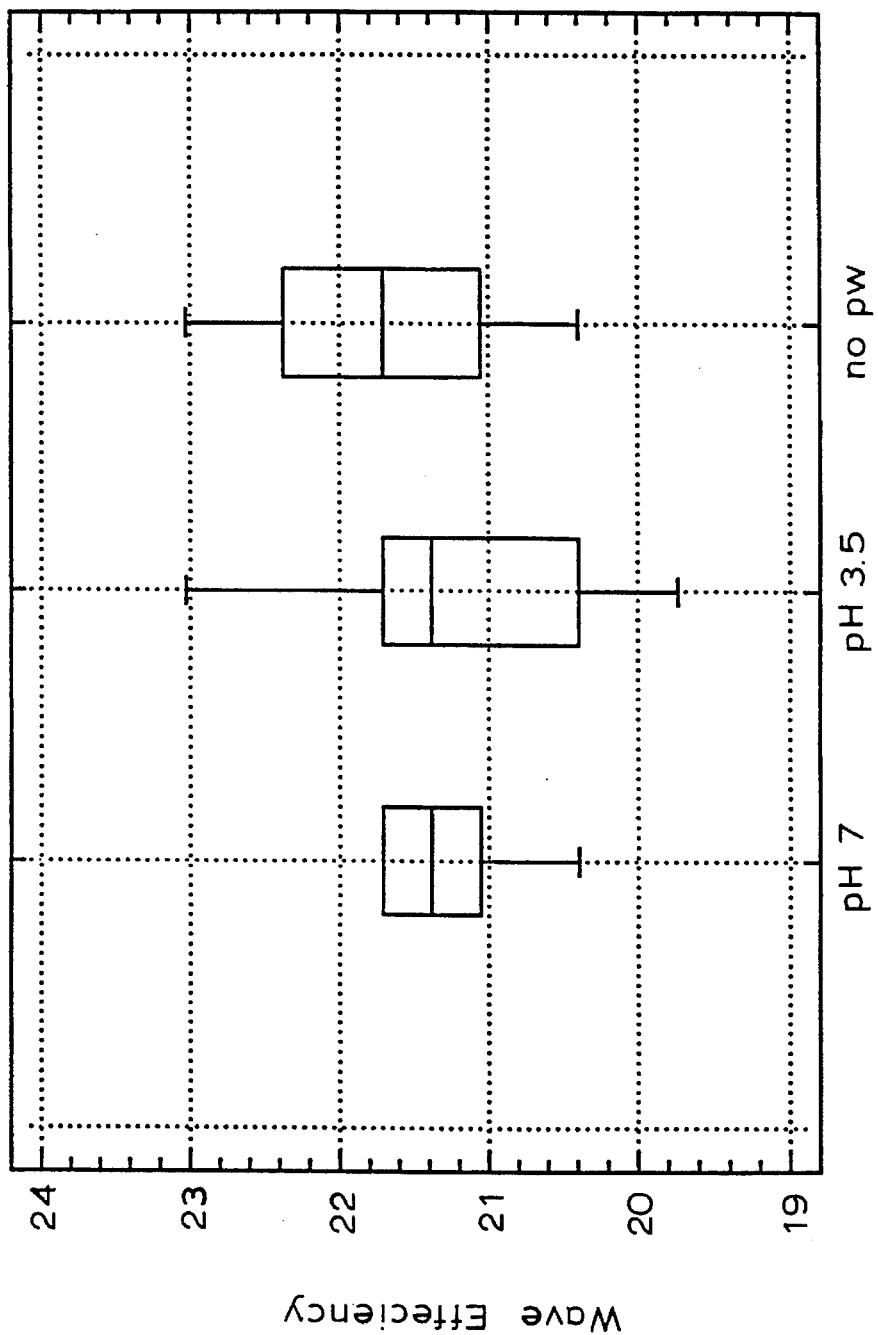

Similar tests were performed using the above formulation of Example 13 (2% Resorcinol; pH=3.5) as a pre-treatment (prewrap) and the same composition, containing 2% by weight resorcinol but at a pH of 7.0, in comparison to no pretreating composition; and then waving the tresses with a monoethanolamine thioglycolate reducing agent-containing formulation. The results, shown in Table IV and in FIG. 5, show essentially no difference between the two prewraps and the no prewrap examples.

TABLE IV

| | R Prewrap | | | | | | | | | | | | |
|---|---|---|---|---|---|---|---|---|---|---|---|---|---|
| Sample Name | Tress 1 Length (cm) | Wave Efficiency (%) | Tress 2 Length (cm) | Wave Efficiency (%) | Tress 3 Length (cm) | Wave Efficiency (%) | Tress 4 Length (cm) | Wave Efficiency (%) | Tress 5 Length (cm) | Wave Efficiency (%) | Tress 6 Length (cm) | Wave Efficiency (%) | Average Tress Length (cm) | Average Wave Efficiency (%) |
| pH-7 | 11.9 | 21.7 | 11.9 | 21.7 | 12.0 | 21.1 | 12.1 | 20.4 | 12.0 | 21.1 | 11.9 | 21.7 | 12.0 | 21.3 |
| pH-3.5 | 12.1 | 20.4 | 12.2 | 19.7 | 12.0 | 21.1 | 11.9 | 21.7 | 11.7 | 23.0 | 11.9 | 21.7 | 12.0 | 21.3 |
| no pre-treat | 11.9 | 21.7 | 11.8 | 22.4 | 11.9 | 21.7 | 12.0 | 21.1 | 12.1 | 20.4 | 11.7 | 23.0 | 11.9 | 21.7 |

Figure 6:
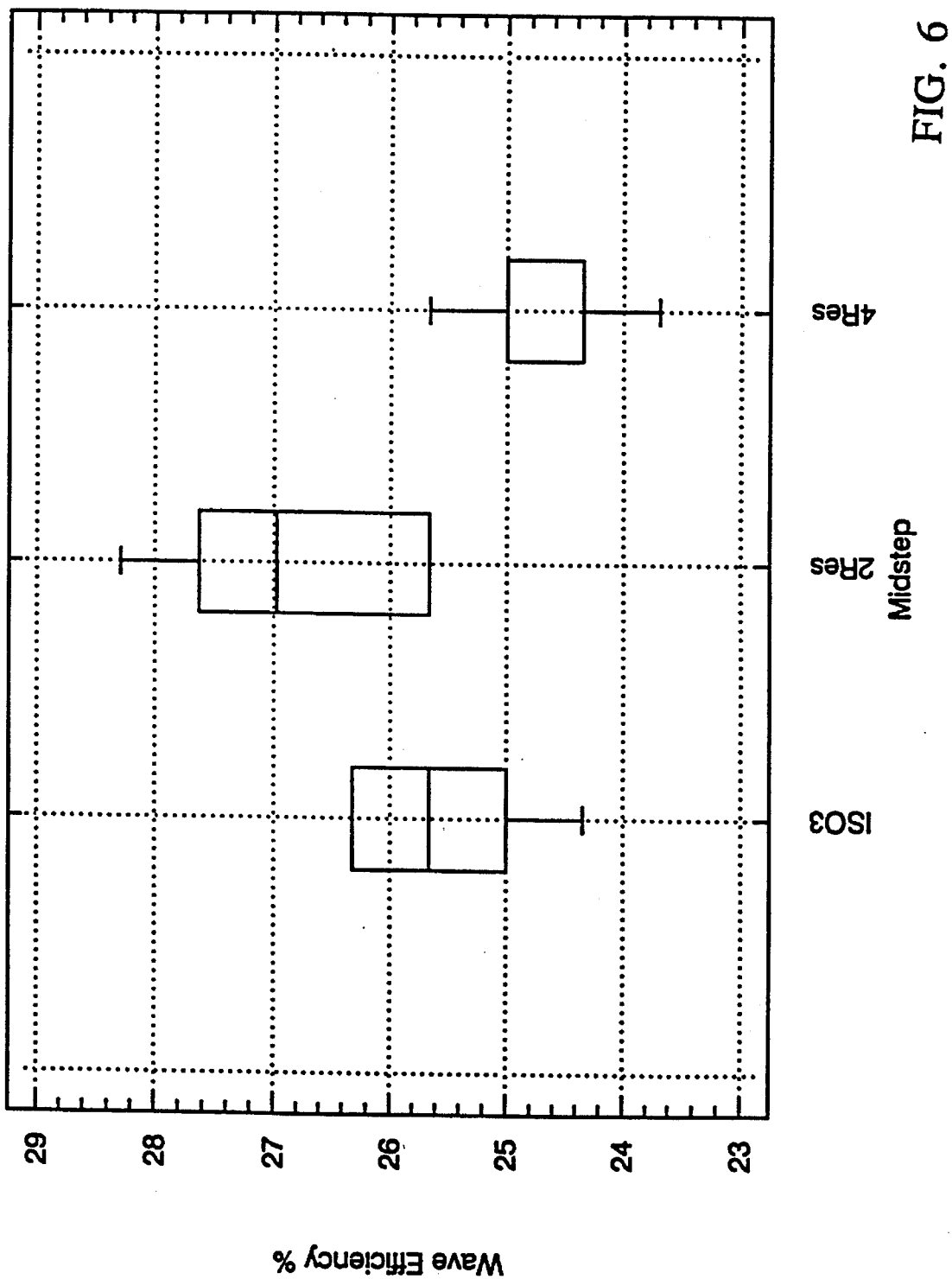

Additional tests were performed using the 2% by weight and 4% by weight resorcinol-containing composition of Examples 2 and 3 as a midstep (after rinsing the waving lotion from the hair) and before the neutralizer ($H_2O_2$-containing) composition in comparison to the use of the second cysteamine-based waving lotion (not followed by the resorcinol-containing composition), as shown in FIG. 6. The data used to derive the graph of FIG. 6 is presented below in Table V:

TABLE V

| Description | Tress 1 Length (cm) | Wave Efficiency (%) | Tress 2 Length (cm) | Wave Efficiency (%) | Tress 3 Length (cm) | Wave Efficiency (%) | Tress 4 Length (cm) | Wave Efficiency (%) | Tress 5 Length (cm) | Wave Efficiency (%) | Tress 6 Length (cm) | Wave Efficiency (%) | Average Tress Length (cm) | Average Wave Efficiency (%) |
|---|---|---|---|---|---|---|---|---|---|---|---|---|---|---|
| Second cysteamine-based waving lotion | 11.2 | 26.3 | 11.3 | 25.7 | 11.2 | 26.3 | 11.3 | 25.7 | 11.4 | 25.0 | 11.5 | 24.3 | 11.3 | 25.55 |
| 2 Res (2%) | 10.9 | 28.3 | 11.0 | 27.6 | 11.0 | 27.6 | 11.2 | 26.3 | 11.3 | 25.7 | 11.3 | 25.7 | 11.1 | 26.87 |
| 4 Res (4%) | 11.4 | 25.0 | 11.3 | 25.7 | 11.4 | 25.0 | 11.5 | 24.3 | 11.4 | 25.0 | 11.6 | 23.7 | 11.4 | 24.78 |

Figure 7:
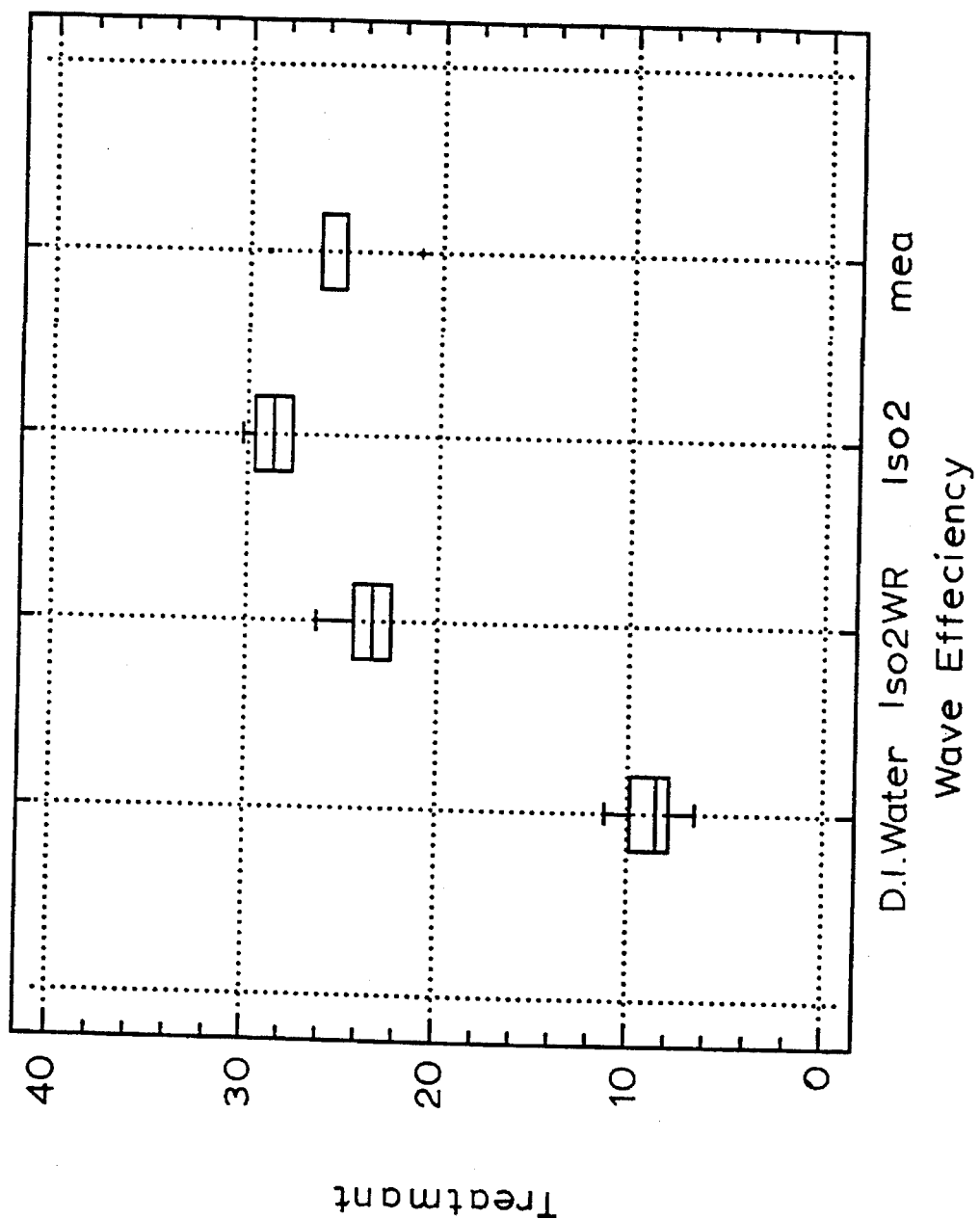

Additional tests were performed using the first cysteamine-based waving lotion and monoethanolamine thioglycolate (MEATG) waving lotions and a pre-treatment composition that included 2% resorcinol (cysteamine WR) in the cysteamine-based waving lotion, and the waving efficiency was calculated from the data of Table VI, to form the graph of FIG. 7:

TABLE VI

| | Prewrap on Normal Hair | | | | | | | | | | | | |
|---|---|---|---|---|---|---|---|---|---|---|---|---|---|
| Sample Name | Tress 1 Length (cm) | Wave Efficiency (%) | Tress 2 Length (cm) | Wave Efficiency (%) | Tress 3 Length (cm) | Wave Efficiency (%) | Tress 4 Length (cm) | Wave Efficiency (%) | Tress 5 Length (cm) | Wave Efficiency (%) | Tress 6 Length (cm) | Wave Efficiency (%) | Average Tress Length (cm) | Average Wave Efficiency (%) |
| DI Water | 13.8 | 9.2 | 14.0 | 7.9 | 14.2 | 6.6 | 14.0 | 7.9 | 13.5 | 11.2 | 13.7 | 9.9 | 13.9 | 8.8 |
| Cysteamine WR | 11.8 | 22.4 | 11.5 | 24.3 | 11.7 | 23.0 | 11.6 | 23.7 | 11.2 | 26.3 | 11.8 | 22.4 | 11.6 | 23.7 |
| Cysteamine | 11.0 | 27.6 | 10.9 | 28.3 | 10.8 | 28.9 | 10.6 | 30.3 | 10.7 | 29.6 | 11.0 | 27.6 | 10.8 | 28.7 |
| MEATG | 10.8 | 28.9 | 11.2 | 26.3 | 11.2 | 26.3 | 11.2 | 26.3 | 11.4 | 25.0 | 12.0 | 21.1 | 11.3 | 25.7 |

Resorcinol-containing compositions at 1% by weight (Example 1) and 2% by weight (Example 2) were applied as a midstep and compared to (1) the first cysteamine-based waving lotion without midstep resorcinol treatment; (2) deionized water midstep treatment, and (3) the first cysteamine-based waving lotion having 8% by weight resorcinol included in the waving lotion (Example 4). The data are shown in Table VII:

TABLE VII

Prewrap on Normal Hair

| Description | Tress 1 Length (cm) | Wave Efficiency (%) | Tress 2 Length (cm) | Wave Efficiency (%) | Tress 3 Length (cm) | Wave Efficiency (%) | Tress 4 Length (cm) | Wave Efficiency (%) | Tress 5 Length (cm) | Wave Efficiency (%) | Tress 6 Length (cm) | Wave Efficiency (%) | Average Tress Length (cm) | Average Wave Efficiency (%) |
|---|---|---|---|---|---|---|---|---|---|---|---|---|---|---|
| First Cysteamine-based waving lotion | 11.3 | 25.7 | 11.5 | 24.3 | 11.5 | 24.3 | 11.0 | 27.6 | 11.7 | 23.0 | 11.8 | 23.4 | 11.5 | 24.7 |
| R Mid 0.73M Cysteamine (Example 2) | 11.2 | 26.3 | 11.3 | 25.7 | 11.4 | 25.0 | | | | | | | 11.3 | 25.7 |
| R Mid 1% Example 1) | 10.5 | 30.9 | 11.3 | 25.7 | 11.0 | 27.6 | | | | | | | 10.9 | 28.1 |
| R 8% in 0.73M Cysteamine (Example 4) | 12.0 | 21.1 | 12.1 | 20.4 | 12.0 | 21.1 | 12.6 | 17.1 | 12.4 | 18.4 | 12.8 | 15.8 | 12.3 | 19.0 |
| DI | 13.6 | 10.5 | 13.7 | 9.9 | 13.6 | 10.5 | 13.5 | 11.2 | 13.6 | 10.5 | 13.5 | 11.2 | 13.6 | 10.6 |

Resorcinol Substantivity

Two gram hair tresses were treated with 2 ml. of the 2% resorcinol solution of Example 2, permed with a standard cysteamine wave (first cysteamine-based waving lotion) and neutralized using the hair tress protocol described (infra). The tresses were then washed 0, 1, 3, and 5 times using the hair tress protocol described (infra).

Residual resorcinol was extracted from the hair by refluxing for one hour in 30 ml. of methanol. The methanol was spiked with 100–200 μg of 2-nonanone and concentrated to one-to-two ml of nitrogen blow-down. Analysis of the extract for resorcinol was by GC-MS. The concentration of resorcinol in the hair after the washings are presented in Table VIII below.

TABLE VIII

| | Resorcinol Remaining In Hair After Washing | | | |
|---|---|---|---|---|
| Treatment | No Wash | 1× wash | 3× wash | 5× wash |
| Resorcinol (ppm) | 650 | 480 | 263 | 180 |

Thus, it can be concluded that substantial amounts of resorcinol remain in the hair even after five shampooings.

Resorcinol Odor Study

A total of 330 models were permed in a large field test of the resorcinol prewrap of Example 13 versus a commercially available prewrap which is purported to reduce cysteamine post-perm odor.

When more than 200 of the models who returned were asked to evaluate their own odor, 17% of the models who had been given the commercially available odor reduction prewrap indicated that they experienced a bad odor while only 12% of the models who where given the resorcinol prewrap indicated that their odor was bad. Three judges trained to recognize the characteristic cysteamine odor also assessed each model upon check-back. Their assessment is presented in Table IX.

TABLE IX

| | Judge Assessment Of Odor | | | |
|---|---|---|---|---|
| | Odor | | | |
| Prewrap | None | Slight | Moderate | High |
| Commercial | 64.0% | 28.3% | 7.7% | 0.0 |
| Resorcinol | 70.8% | 24.0% | 5.2% | 0.0 |

Overall it can be concluded that the resorcinol prewrap is better at reducing the characteristic post-perm odor that occurs with cysteamine than the treatment that is currently commercially available.

PROTOCOL

Tress Washing Procedure:

1. Soak the hair for 10 minutes in a 15% by weight aqueous solution of sodium lauryl sulfate (SLS) at a pH of 7.5 to remove residual cationics from the untreated hair.
2. Stroke the hair 20 times in one (1) minute to insure that all of the hair fibers have been thoroughly treated with SLS.
3. Rinse the hair for one minute at 40° C. (approximate body temperature) using the rinse apparatus. Make sure that the hair is thoroughly rinsed but do not physically manipulate it.
4. Soak the hair for 10 minutes in a 10% by weight Triton, X-100/10% by weight isopropyl alcohol/80% by weight deionized water solution to remove organic contaminants such as napthalenes.
5. Stroke the hair 20 times in one (1) minute to insure that all of the hair fibers have been thoroughly treated with the solution.
6. Rinse the hair for one (1) minute at 40° C. using the rinse apparatus. Make sure that the hair is thoroughly rinsed but do not physically manipulate it.
7. The hair is now ready for testing product performance or deposition.

Pretreatment of Hair Tresses for Measuring Product Performance:

1. Prewash hair.
2. Dampen the prewashed hair under the rinse apparatus.
3. Apply product directly to hair according to the salon recommended amounts for the type of product you are testing:
   Shampoo or 2 in 1 Shampoo: 10 mL Product/100 g Hair (example: for a 2 g tress, use 0.2 mL of product)
   Conditioner: 30 mL Product/100 g Hair (example: for a 2 g tress, use 0.6 mL of product).
4. Massage the product into the hair for one (1) minute (20 strokes).
5. Rinse the hair for 30 seconds for 2 in 1 shampoos and conditioners or one (1) minute for shampoos. Use the rinse apparatus set at 40° C. for rinsing the hair. Thoroughly rinse the hair, but do not physically manipulate it.
6. Allow the hair to dry under the hot-air dryer.
7. At this point the hair is ready for analysis if a one time treatment study is requested. Steps 2 through 6 are repeated when a multi-treatment or build-up study is requested.

Note: When a conditioner is being treated for more than one time, a washing step must be added between conditioning treatments. The washing step is usually done with the companion shampoo when available.

Processing of Hair Tresses:

1. Utilize only stripped tresses and rinse each tress separately for 60 seconds at 38° C.
2. Apply 2×100 µl of cysteamine-based wave lotion across each tress and place into plastic processing cap. Close cap with small binder clip and process for 20 minutes at 38° C.
3. Rinse tresses for 60 seconds with 38° C. tap water.
4. Towel blot tresses until no water spots appear.
5. Apply 2×100 µl of a 2.2% hydrogen peroxide, pH 3.5 and process 5 minutes inside plastic wave cap at 38° C.
6. Rinse tresses for 60 seconds at 38° C. with tap water and place on paper towel.
7. After spraying tress 10× with DI water bottle, insert tress into glass jar and incubate at 50° C. overnight. If performing a time study, it is crucial that tresses after the first day are dried before incubating in the oven. This is done to help prevent microbiological growth.
8. Tresses are next re-wet in 50° C. water for an odor panel or ready for further performance testing. The cysteamine-based waving lotion is included as a control for post-perm odor. (Include DI as well.)

PROTOCOL

APPARATUS

Bath: 5 gallon, 30° C., equipped with:
Tank—cylindrical with spigot for draw-off, Nalgene or equivalent
Circulator—constant temperature immersion, Haake E3 or equivalent
Pump—Little Giant Model 2E-N or equivalent
Sensors—(3) connected to Martron Liquid Level Switch Model 14-03 or equivalent
Valve: water flow control
Footswitch
Comb: Eagle#185 hard rubber or equivalent
Syringe: Luer Lok B-D, 1 cc, disposable Block: hair cutting, consisting of a wooden block 3⅜"× 11¾×1½" with cold wave clamp attached to one end and with marks indicating 6", 7" and 8" for cutting tresses to desired length.
Scissors: stainless steel, 5" blade
Hole
Puncher: ¼" or equivalent

REAGENTS

Hair: DeMeo normal untreated standard tresses and/or laboratory bleach-waved tresses.

PROCEDURE

A. Preparation of Tresses
1. Clamp tress on cutting block.
2. Hold lower part of tress flat between the forefinger and middle finger.
3. Cut across the tress at the 6" mark.
4. Remove the tress from the block.
5. Punch a hole at the top of the tress tab.

Numerous modifications and alternative embodiments of the invention will be apparent to those skilled in the art in view of the foregoing description. Accordingly, this description is to be construed as illustrative only and is for the purpose of teaching those skilled in the art the best mode of carrying out the invention. The details of the structure may be varied substantially without departing from the spirit of the invention, and the exclusive use of all modifications which come within the scope of the appended claims is reserved.

What is claimed is:

1. A composition effective in reducing malodor resulting from contacting hair with a disulfide bond-breaking reducing agent in a waving lotion used in permanent waving comprising:

an aqueous solution of a polyhydric phenol, reactive with hair aldehydes, having the formula I:

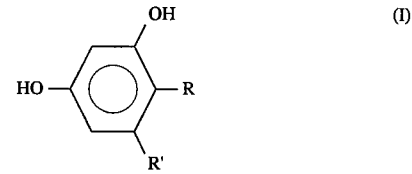

wherein
R'=H or OH,
R=H or $C_1$–$C_{12}$ alkyl,
$C_1$–$C_{12}$ alcohol,
$C_1$–$C_{12}$ aldehyde, or
a ketone having formula (II)

wherein
n=0–12, R"=$C_1$–$C_{12}$ alkyl, and wherein n+number of carbons in R"=1–12,
said polyhydric phenol having a concentration in the range of about 0.05% to about 10% by weight, and said composition having a pH in the range of about 1.5 to about 10.

2. The composition of claim 1, wherein the concentration of polyhydric phenol is in the range of about 0.1% to about 5% by weight.

3. The composition of claim 2, wherein the concentration of polyhydric phenol is in the range of about 1% to about 5% by weight.

4. The composition of claim 3, wherein the concentration of polyhydric phenol is in the range of about 1.5% to about 2.5% by weight.

5. The composition of claim 4, wherein the concentration of polyhdric phenol is about 2% by weight.

6. The composition of claim 1, wherein the pH is in the range of about 1.5 to about 8.5.

7. The composition of claim 6, wherein the pH is in the range of about 3.5 to about 7.0.

8. The composition of claim 1, wherein the composition includes a surfactant in an amount of about 1.0% to about 20% by weight.

9. The composition of claim 1, wherein the composition further includes a hair conditioner in an amount of about 0.1% to 10% by weight.

10. The composition of claim 8, wherein the composition further includes a hair conditioner in an amount of about 0.5% to 5% by weight.

11. The composition of claim 1, further including a reducing agent capable of breaking hair disulfide bonds, said reducing agent included in an amount of about 1% to about 20% by weight.

12. The composition of claim 11, wherein the reducing agent is selected from the group consisting of a cysteamine, a derivative of cysteamine, a monothioglycolate, a derivative of a monthioglyolate, a bisulfite, and mixtures thereof.

13. The composition of claim 1, wherein the polyhydric phenol is selected from the group consisting of resorcinol, hexyl resorcinol, acetaldehyde resorcinol, catechol, hydroquinone, pyroyallol, phloroglucinol, 1-nepthol, 4-chloroesorcinol, m-phenylene-diamine, and 2-methyl-5-amino phenol.

14. The composition of claim 13, wherein the polyhydric phenol is selected from the group consisting of resorcinol, hexyl resorcinol and acetaldehyde resorcinol.

15. The composition of claim 14, wherein the polyhydric phenol is resorcinol.

16. A method of reducing malodor resulting from breaking disulfide bonds in the hair sufficiently such that the configuration of the hair and the hair disulfide bonds are reestablished in a different configuration after neutralizing the hair by contact with oxidizing agent comprising;

contacting the hair with a disulfide bond-breaking reducing agent to break a sufficient number of hair disulfide bonds such that the hair can be reconfigured in a different configuration by subsequently contacting the hair, while in the different configuration, with an oxidizing agent;

subsequently gontacting the hair with an oxidizing agent, to reform the broken disulfide bonds, while the hair is in the different configuration;

contacting the hair with an aqueous composition including a polyhydric phenol, that is reactive with a hair aldehyde, having the formula I:

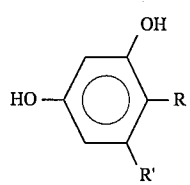

wherein
R'=H or OH,
R=H or $C_1$–$C_{12}$ alkyl,
$C_1$–$C_{12}$ alcohol,
$C_1$–$C_{12}$ aldehyde, or
a ketone having formula (II)

$$-(CH_2)_n-\overset{O}{\underset{\|}{C}}-R'' \qquad (II)$$

wherein
n=0–12, R"=$C_1$–$C_{12}$ alkyl, and wherein n+number of carbons in R"=1–12, said polyhydric phenol having a concentration in said composition in the range of about 0.05% to about 10% by weight, and said composition having a pH in the range of about 1.5 to about 10;

wherein the hair is contacted with the polyhydric phenol; at a process step selected from the group consisting of (a), (b), (c) and (d), as follows:

(a) before contacting the hair with the disulfide bond-breaking reducing agent;

(b) together with the disulfide bond-breaking reducing agent;

(c) between contacting the hair with the disulfide bond-breaking reducing agent, and contacting the hair with the oxidizing agent; and (d) after neutralizing the disulfide bond-breaking reducing agent with the oxidizing agent.

17. The method of claim 16, wherein the hair is contacted with said aqueous composition before contacting the hair with the disulfide bond-breaking reducing agent.

18. The method of claim 16, wherein the hair is contacted with said aqueous composition after contacting the hair with the disulfide bond-breaking reducing agent.

19. The method of claim 16, wherein the hair is contacted with said aqueous composition after contacting the hair with the disulfide bond-breaking reducing agent, and after rinsing the reducing agent from the hair.

20. The method of claim 18, wherein the aqueous composition contacts the hair simultaneously with contacting the hair with the disulfide bond-breaking reducing agent.

21. The method of claim 18, wherein the hair is contacted with the aqueous composition after the disulfide bond-breaking reducing agent applied to the hair has been neutralized with the oxidizing agent.

22. The method of claim 21, wherein the hair is contacted with the aqueous composition after the oxidizing agent has been rinsed from the hair.

23. The method of claim 16, wherein the aqueous composition containing the polyhydric phenol contains the polyhydric phenol in a concentration of about 0.5% to about 10% by weight.

24. The method of claim 23, wherein the aqueous composition containing the polyhydric phenol contains the polyhydric phenol in a concentration of about 1.0% to about 5% by weight.

25. The method of claim 24, wherein the aqueous composition containing the polyhydric phenol contains the polyhydric phenol in a concentration of about 1.54 to about 2.5% by weight.

26. The method of claim 25, wherein the aqueous composition containing the polyhydric phenol contains the polyhydric phenol in a concentration of about 2% by weight.

* * * * *